US00PP29848P2

(12) United States Plant Patent
Arts

(10) Patent No.: US PP29,848 P2
(45) Date of Patent: Nov. 20, 2018

(54) ***MANDEVILLA* PLANT NAMED 'MAN216902'**

(50) Latin Name: *Mandevilla sanderi*
Varietal Denomination: MAN216902

(71) Applicant: Niels Arts, Aalsmeer (NL)

(72) Inventor: Niels Arts, Aalsmeer (NL)

(73) Assignee: MBA B.V., De Kwakel (NL)

( * ) Notice: Subject to any disclaimer, the term of this patent is extended or adjusted under 35 U.S.C. 154(b) by 10 days.

(21) Appl. No.: 15/731,198

(22) Filed: May 1, 2017

(51) Int. Cl.
*A01H 5/02* (2018.01)

(52) U.S. Cl.
USPC ..... Plt./232
CPC ..... *A01H 5/02* (2013.01)

(58) Field of Classification Search
USPC ..... Plt./226, 232
See application file for complete search history.

*Primary Examiner* — Susan McCormick Ewoldt
*Assistant Examiner* — Karen M Redden
(74) *Attorney, Agent, or Firm* — C. A. Whealy

(57) ABSTRACT

A new and distinct cultivar of *Mandevilla* plant named 'MAN216902', characterized by its relatively compact, upright and spreading plant habit; vigorous growth habit; freely branching habit; relatively small glossy green-colored leaves; early and freely flowering habit; and large bright red-colored flowers.

2 Drawing Sheets

Botanical designation: *Mandevilla sanderi.*
Cultivar denomination: 'MAN216902'.

BACKGROUND OF THE INVENTION

The present invention relates to a new and distinct cultivar of *Mandevilla* plant, botanically known as *Mandevilla sanderi* and hereinafter referred to by the name 'MAN216902'.

The new *Mandevilla* plant is a product of a planned breeding program conducted by the Inventor in De Kwakel, The Netherlands. The objective of the breeding program is to create new freely-flowering *Mandevilla* plants with large and attractive flowers.

The new *Mandevilla* plant originated from a cross-pollination conducted by the Inventor in De Kwakel, The Netherlands in August, 2012 of a proprietary selection of *Mandevilla sanderi* identified as code number 11-0008-000, not patented, as the female, or seed parent with a proprietary selection of *Mandevilla sanderi* identified as code number 11-0007-000, not patented, as the male, or pollen, parent. The new *Mandevilla* plant was discovered and selected by the Inventor as a single flowering plant from within the progeny of the stated cross-pollination in a controlled greenhouse environment in De Kwakel, The Netherlands in May, 2015.

Asexual reproduction of the new *Mandevilla* plant by vegetative cuttings in a controlled greenhouse environment in De Kwakel, The Netherlands, since August, 2015 has shown that the unique features of this new *Mandevilla* plant are stable and reproduced true to type in successive generations.

SUMMARY OF THE INVENTION

Plants of the new *Mandevilla* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'MAN216902'. These characteristics in combination distinguish 'MAN216902' as a new and distinct *Mandevilla* plant:

1. Relatively compact, upright and spreading plant habit.
2. Vigorous growth habit.
3. Freely branching habit.
4. Relatively small glossy green-colored leaves.
5. Early and freely flowering habit.
6. Large bright red-colored flowers.

Plants of the new *Mandevilla* can be compared to plants of the female parent selection. Plants of the new *Mandevilla* differ primarily from plants of the female parent selection in flower color as plants of the female parent selection have pinkish red-colored flowers.

Plants of the new *Mandevilla* can be compared to plants of the male parent selection. Plants of the new *Mandevilla* differ primarily from plants of the male parent selection in flowering habit as plants of the new *Mandevilla* are more freely flowering than plants of the male parent selection.

Plants of the new *Mandevilla* can be compared to plants of *Mandevilla atroviolacea* X (*Mandevilla amabilis* X *Mandevilla boliviensis*) 'Sunmandecrim', disclosed in U.S. Plant Pat. No. 15,539. In side-by-side comparisons, plants of the new *Mandevilla* differ primarily from plants 'Sunmandecrim' in the following characteristics:

1. Plants of the new *Mandevilla* are more compact and have shorter internodes than plants of 'Sunmandecrim'.
2. Plants of the new *Mandevilla* flower earlier than plants of 'Sunmandecrim'.
3. Plants of the new *Mandevilla* are more freely flowering than plants of 'Sunmandecrim'.

BRIEF DESCRIPTION OF THE PHOTOGRAPHS

The accompanying colored photographs illustrate the overall appearance of the new *Mandevilla* plant showing the colors as true as it is reasonably possible to obtain in colored reproductions of this type. Colors in the photographs may differ slightly from the color values cited in the detailed botanical description which accurately describe the actual colors of the new *Mandevilla* plant.

The photograph on the first sheet is a side perspective view of typical 7-month old flowering plants of 'MAN216902' grown in round containers with one plant per 10-cm container.

The photograph on the second sheet is side perspective view of typical 9-month old flowering plants of 'MAN216902' grown in a 24-cm patio container with nine plants per container.

DETAILED BOTANICAL DESCRIPTION

The aforementioned photographs and following observations, measurements and values describe plants grown during the autumn, winter and spring in a glass-covered greenhouse in De Kwakel, The Netherlands and under cultural practices typical of *Mandevilla* commercial production. During the production of the plants, day temperatures ranged from 20° C. to 22° C. and night temperatures averaged 18° C. Plants were pinched one time four weeks after planting. Plants were seven and nine months old when the photographs were taken and eight months old when the description was taken. In the following description, color references are made to The Royal Horticultural Society Colour Chart, 2015 Edition, except where general terms of ordinary dictionary significance are used.

Botanical classification: *Mandevilla sanderi* 'MAN216902'.

Parentage:

- *Female, or seed, parent*.—Proprietary selection of *Mandevilla sanderi* identified as code number 11-0008-000, not patented.
- *Male, or pollen, parent*.—Proprietary selection of *Mandevilla sanderi* identified as code number 11-0007-000, not patented.

Propagation:

- *Type*.—By vegetative cuttings.
- *Time to initiate roots, summer*.—About 21 days at temperatures about 22° C.
- *Time to initiate roots, winter*.—About 27 days at temperatures about 22° C.
- *Time to produce a rooted young plant, summer*.—About 40 days at temperatures about 22° C.
- *Time to produce a rooted young plant, winter*.—About 50 days at temperatures about 22° C.
- *Root description*.—Medium in thickness, fibrous to slightly fleshy; typically whitish brown in color, actual color of the roots is dependent on substrate composition, water quality, fertilizers, substrate temperature and physiological age of roots.
- *Rooting habit*.—Freely branching; dense.

Plant description:

- *Plant and growth habit*.—Relatively compact, upright and spreading plant habit; short internodes, dense and bushy appearance; vigorous growth habit; moderately rapid growth rate.
- *Plant height, soil level to top of foliar plane*.—About 21 cm.
- *Plant height, soil level to top of floral plane*.—About 21 cm.
- *Plant diameter* (*spread*).—About 22 cm.
- *Lateral branch description*.—Branching habit: Freely branching habit with about two primary each with about two secondary lateral branches developing per plant. Length, primary branches: About 15 cm to 20 cm. Length, secondary branches: About 5 cm to 10 cm. Diameter, primary and secondary branches: About 3 mm. Internode length: About 2 cm to 3 cm. Strength: Strong. Texture and luster: Smooth, glabrous; semi-glossy becoming woody and matte with development. Color, developing: Close to 144B. Color, developed: Close to 144A; when woody, close to 148B.

Leaf description:

- *Arrangement*.—Opposite, simple; relatively small.
- *Length*.—About 3 cm to 5 cm.
- *Width*.—About 3 cm to 4 cm.
- *Shape*.—Ovate.
- *Apex*.—Mucronate.
- *Base*.—Slightly cordate.
- *Margin*.—Entire.
- *Texture and luster, upper and lower surfaces*.—Smooth, glabrous; leathery; glossy.
- *Venation pattern*.—Pinnate.
- *Color*.—Developing leaves, upper and lower surfaces: Close to 137D. Full expanded leaves, upper surface: Close to NN137A; main vein, close to 143C and lateral venation, close to NN137A. Fully expanded leaves, lower surface: Close to 146C; main vein, close to 143C and lateral venation, close to 146C.
- *Petioles*.—Length: About 1 cm to 1.5 cm. Diameter: About 2 mm. Strength: Strong. Texture and luster, upper and lower surfaces: Smooth, glabrous; semi-glossy. Color, upper surface: Close to 181B. Color, lower surface: Close to 144B.

Flower description:

- *Flower type and flowering habit*.—Single salverform flowers arranged in axillary racemes; flowers star-shaped and face upright to outwardly; freely flowering habit with about five to six flowers per inflorescence and during the flowering season, about 25 flower buds and flowers per plant at one time.
- *Natural flowering season*.—Plants flower continuously from spring until frost in The Netherlands; plants begin flowering about seven months after planting.
- *Flower longevity on the plant*.—About eight to ten days; flowers not persistent.
- *Fragrance*.—None detected.
- *Inflorescence height*.—About 10 cm.
- *Inflorescence diameter*.—About 15 cm.
- *Flower buds*.—Length: About 8 cm. Diameter: About 1.2 cm. Shape: Elongated spindle-shaped. Texture and luster: Smooth, glabrous; semi-glossy. Color: Close to N144D and 181D; towards the base, close to 184C.
- *Flowers*.—Appearance: Flared trumpet, corolla fused and five-parted. Diameter: About 8 cm to 9 cm. Depth (length): About 4 cm to 6 cm. Throat diameter: About 1.8 cm. Tube length: About 3 cm to 4 cm. Tube diameter, distally: About 4 mm.
- *Corolla*.—Quantity and arrangement: Five petals arranged in a single whorl; proximal portion of the petals are fused into a tube; distal free portions slightly imbricate. Petal length: About 4 cm. Petal width: About 3 cm to 3.5 cm. Petal shape and appearance: Ovate to triangular, asymmetrical. Petal apex: Acute. Petal margin: Entire; slightly undulate. Petal texture and luster, upper and lower surfaces: Smooth, glabrous; semi-glossy. Throat and tube texture: Smooth, glabrous. Color: Petal, when opening, upper surface: Close to 46C. Petal, when opening, lower surface: Close to N45D; stripe, close to 155D. Petal, fully opened, upper surface: Close to 46B; venation, close to 46B; color does not change with development. Petal, fully opened, lower surface: Close to N45D; stripe, close to 155D; venation, close to N45D; color does not change with development. Throat: Close to 30C; venation, close to 30C. Tube: Close to between 181D and 184C; towards the base, close to N144D; stripe, close to 155D; venation, same as ground colors.

*Calyx*.—Quantity and arrangement: Five sepals arranged in a single whorl; calyx, star-shaped. Length: About 5 mm to 8 mm. Diameter: About 4 mm to 6 mm. Sepal length: About 4 mm to 6 mm. Sepal width: About 2 mm. Sepal shape: Subulate. Sepal apex: Acute. Sepal margin: Entire. Sepal texture and luster, upper and lower surfaces: Smooth, glabrous; semi-glossy. Sepal color: When opening, upper and lower surfaces: Close to 145A. Fully opened, upper and lower surfaces: Close to 145A.

*Peduncles*.—Length: About 3 cm to 4 cm. Diameter: About 2 mm to 3 mm. Strength: Strong. Aspect: Mostly upright. Texture and luster: Smooth, glabrous; glossy. Color: Close to 146D.

*Pedicels*.—Length: About 2 cm. Diameter: About 3 mm. Strength: Strong. Aspect: Upright to about 30° from peduncle axis. Texture and luster: Smooth, glabrous; glossy. Color: Close to 144C.

*Reproductive organs*.—Stamens: Quantity and arrangement: Typically five; basifixed; anthers connivent. Filament color: Close to 14D. Anther length: About 6 mm to 8 mm. Anther shape: Narrowly oblong. Anther color: Close to 14D. Pollen amount: Moderate. Pollen color: Close to 14D. Pistils: Quantity: Typically one. Pistil length: About 1 cm to 1.5 cm. Style color: Close to 150B. Stigma shape: Club-shaped. Stigma diameter: About 2 mm. Stigma color: Close to 150D. Ovary color: Close to 144A.

*Seeds*.—Quantity per flower: About 200. Length: About 7 mm. Diameter: About 1 mm. Texture: Smooth, glabrous. Color: Brownish, close to 200D.

Disease & pest resistance: Plants of the new *Mandevilla* have not been noted to be resistant to pathogens and pests common to *Mandevilla* plants.

Temperature tolerance: Plants of the new *Mandevilla* have been observed to tolerate temperatures ranging from about 1° C. to about 45° C.

It is claimed:

1. A new and distinct *Mandevilla* plant named 'MAN216902' as illustrated and described.

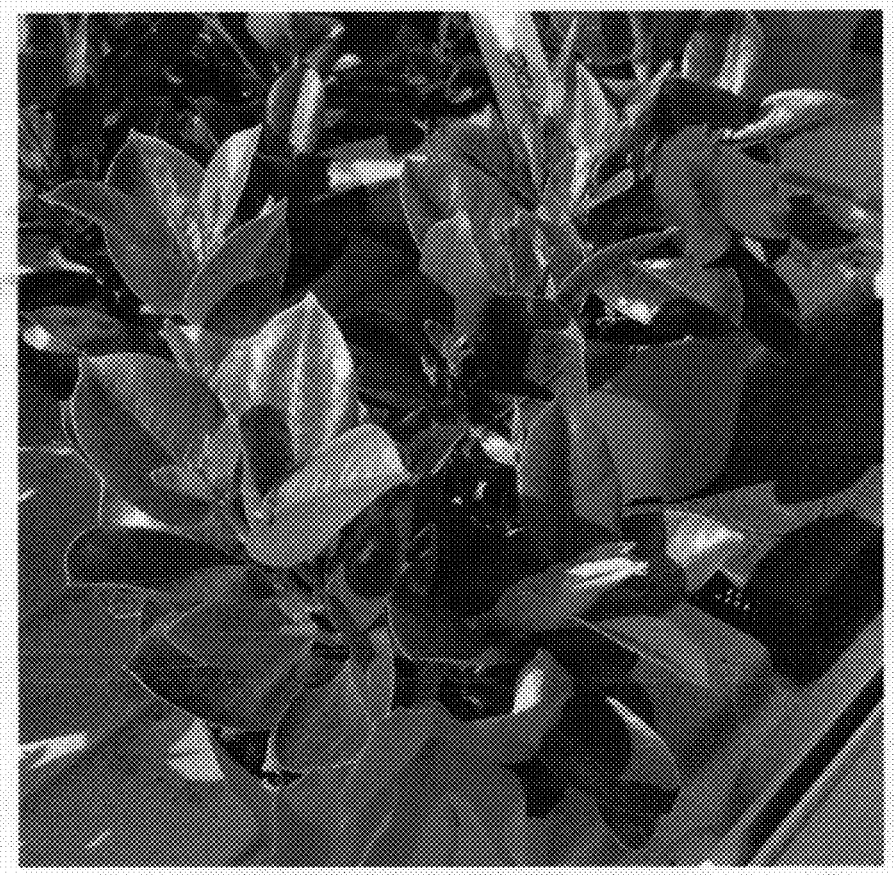

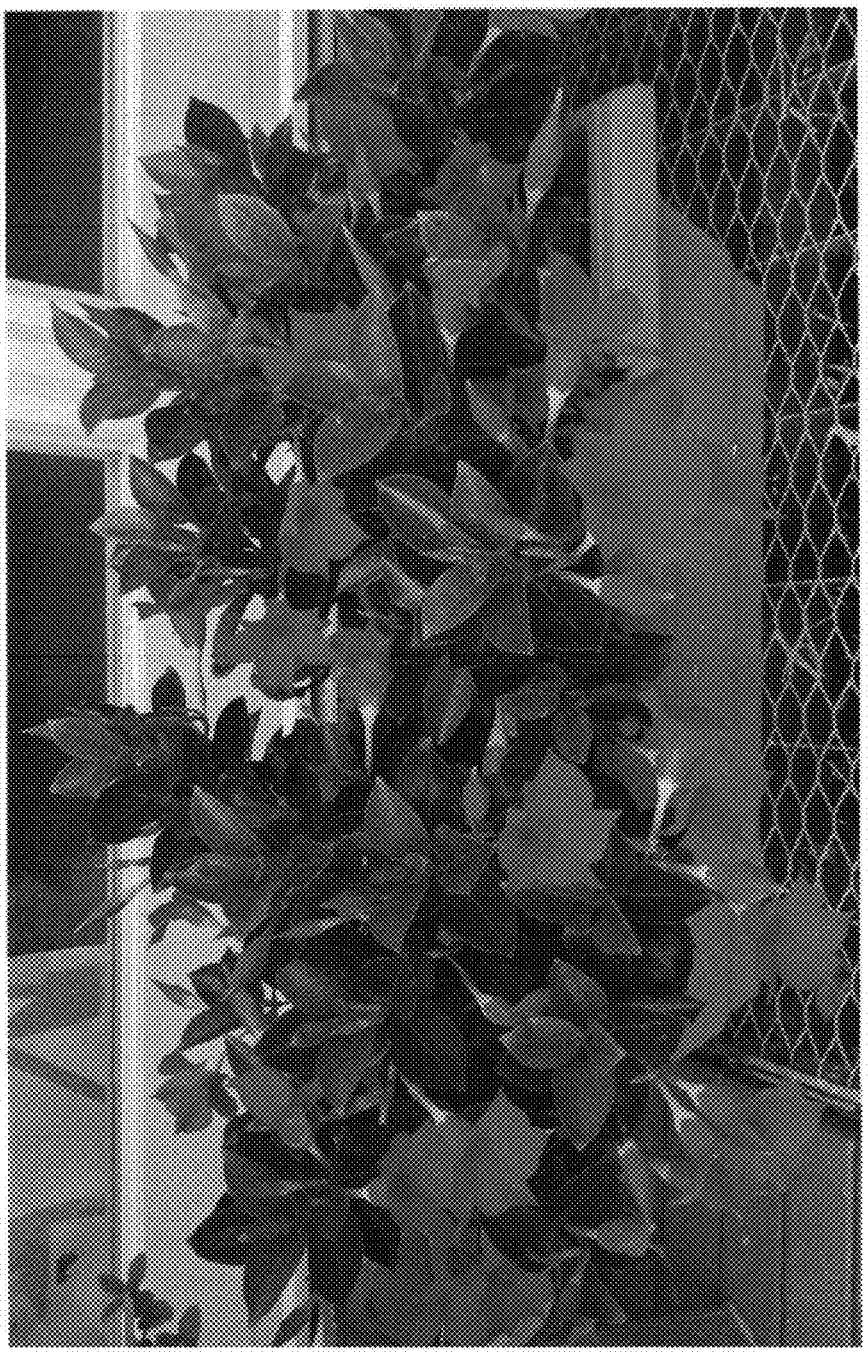

* * * * *